United States Patent [19]

Spector

[11] Patent Number: 4,720,409

[45] Date of Patent: Jan. 19, 1988

[54] FILM-LAMINATE TYPE AIR FRESHENER

[76] Inventor: Donald Spector, 380 Mountain Rd., Union City, N.J. 07087

[21] Appl. No.: 16,109

[22] Filed: Feb. 18, 1987

Related U.S. Application Data

[63] Continuation-in-part of Ser. No. 932,610, Nov. 20, 1986, Pat. No. 4,696,844.

[51] Int. Cl.$^4$ .............................. B32B 3/14; B44C 1/28
[52] U.S. Cl. ........................................ 428/46; 239/54; 239/289; 428/40; 428/49; 428/905
[58] Field of Search .................... 428/46, 49, 79, 905, 428/13, 40, 48; 239/34, 54, 289

[56] References Cited

U.S. PATENT DOCUMENTS

| | | | |
|---|---|---|---|
| 2,169,055 | 8/1939 | Overshiner | 428/905 X |
| 2,577,320 | 12/1951 | Fenyo | 428/905 X |
| 2,987,103 | 6/1961 | Yakubik | 428/203 |
| 3,216,882 | 11/1965 | Feldt et al. | 428/522 X |
| 3,578,545 | 5/1971 | Carson et al. | 428/905 X |
| 3,655,129 | 4/1972 | Selner | 428/905 X |
| 3,685,734 | 8/1972 | Paciorek et al. | 428/905 X |
| 3,994,439 | 11/1976 | Van Breen et al. | 428/905 X |
| 4,051,159 | 9/1977 | Tsoucalas et al. | 428/905 X |
| 4,077,926 | 3/1978 | Sanderson et al. | 428/463 X |
| 4,277,024 | 7/1981 | Spector | 428/905 X |
| 4,283,011 | 8/1981 | Spector | 428/79 X |
| 4,401,703 | 8/1983 | Rodgers | 428/47 X |
| 4,418,099 | 11/1983 | Cuevas et al. | 427/229 |
| 4,419,396 | 12/1983 | Sugimoto | 428/905 X |
| 4,493,869 | 1/1985 | Sweeny et al. | 428/79 X |
| 4,547,122 | 10/1985 | Leech | 428/49 X |
| 4,555,438 | 11/1985 | Orsak et al. | 428/905 X |
| 4,580,581 | 4/1986 | Reece et al. | 239/289 X |
| 4,594,218 | 4/1986 | Travis | 428/79 X |

*Primary Examiner*—Henry F. Epstein
*Attorney, Agent, or Firm*—Michael Ebert

[57] ABSTRACT

A replaceable air freshener primarily for use on the tiled wall of a bathroom or kitchen. The air freshener is formed by a transparent plastic face film laminated to a transparent plastic backing film to create a laminate whose dimensions match those of a standard tile. The rear surface of the backing film has a low tack, clear adhesive thereon whereby the laminate may be adhered to a selected tile on the wall or readily removed therefrom. The face film is constituted by a polymeric matrix having myriad cells dispersed therein impregnated with a volatile fragrance which is slowly released from the face film into the atmosphere of the room. Screened on the front surface of the backing film is an artwork which is visible through the face film and has a background field imparted thereto by the color of the tile onto which the laminate is adhered so that the artwork is then in harmony with the tiled wall. The emitted fragrance from the face film is thematically released to the artwork so that should the artwork be the Xmas tree, the fragrance will be that of pine.

7 Claims, 5 Drawing Figures

FILM-LAMINATE TYPE AIR FRESHENER

RELATED APPLICATION

This application is a continuation-in-part of my pending application Ser. No. 932,610, now U.S. Pat. No. 4,696,844, filed Nov. 20, 1986, entitled "Film Type Air Freshener," the entire disclosure of which is incorporated herein by reference.

BACKGROUND OF INVENTION

1. Field of Invention

This invention relates generally to air fresheners which release an aroma into the atmosphere of a room, and more particularly to a replaceable air freshener in the form of a film laminate which is adhered to a wall tile and which emits an aroma that is thematically related to an artwork screened on one film of the laminate.

2. Status of Prior Art

As used herein, the term "aroma" or "fragrance" is not limited to perfume-like odors, but encompasses any odor that is suitable as an air freshener to condition, modify or otherwise charge the ambient atmosphere.

The aroma of perfumes and perfume-based products such as colognes and toilet waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

The environment of a kitchen or bathroom may be rendered unpleasant by food and cooking smells as well as toilet and other pungent odors. The common practice, therefore, is to mask or modify the prevailing atmosphere by some sort of air freshener.

It is known to provide an air freshener or fragrance generator in the form of a bottle containing a volatile liquid in which a wick is immersed, the upper end of the wick extending above the bottle and being exposed to the air. Such devices are subject to spillage or leakage; and in order to adjust the rate of volatilization, means must be provided to vary the extent of wick exposure.

The typical commercial air freshener has a strictly utilitarian appearance which clashes with many household decors. It is for this reason that a commercial air freshener is often placed where it is out of sight. On the other hand, an air freshener is most effective when placed in an exposed open area where it is subjected to maximum air flow. By hiding the air freshener in a confined area, one whereby renders it less effective for its intended function, which is to permeate the prevailing atmosphere with a pleasing fragrance.

The present invention provides an air freshener which by its very nature is located at an open area where it is exposed to a free flow of air, the freshener making use of a film of polymeric material impregnated with a volatile fragrance. The concept of gradually releasing a volatile fragrance over an extended period of time from a plastic film is well known and is disclosed, for example, in U.S. Pat. No. 2,169,055. In this patent, a fragrance emitting film is produced by mixing essential oils and a solvent therefor into a cellulose acetate solution from which films are formed, the solvent for the oils being quickly evaporated, after which the essential oils slowly volatilize.

Various other forms of controlled fragrance films are disclosed in the following U.S. Pat. Nos.
4,419,396
4,051,159
3,994,439
3,685,734
3,655,129

My above-identified copending application discloses a replaceable air freshener primarily for use on the tiled wall of a bathroom or kitchen. The air freshener is formed by a transparent plastic film of polymeric material whose dimensions match those of a standard tile, the rear face of the film having a low tack, clear adhesive thereon whereby the film may be laminated to a selected tile on the wall or readily removed therefrom.

The film is constituted by a polymeric matrix having myriad cells dispersed therein impregnated with a volatile fragrance which is slowly released from the film into the atmosphere of the room. Screened on the front face of the film is an artwork having a background field imparted thereto by the color of the tile onto which the film is laminated so that the artwork is then in harmony with the tiled wall. The emitted fragrance is thematically related to the artwork so that should the artwork be an Xmas tree, the fragrance will be that of pine.

Because the film is impregnated and is not a conventional polymeric film, some difficulty is experienced in screening artwork on the front face of this film so that the artwork is permanently formed thereon and is not degraded by moist and warm ambient air which is normally found in the atmosphere of a kitchen or bathroom: Moreover, because the artwork is on the front face, it is subject to being rubbed off by those who rub against the tiles to which the film is laminated.

SUMMARY OF INVENTION

The primary object of this invention is to provide an improved air freshener which also is a work of art and therefore can be conspicuously placed at an open site that is conducive to the most effective operation of the air freshener, the fragrance emanating from the air freshener being thematically related to the artwork displayed thereby so that a viewer's visual impression thereof is accompanied by an olfactory impression which enhances the enjoyment of the work.

More particularly, an object of the invention is to provide an air freshener in the form of a film laminate in which the artwork is screened onto the front surface of a transparent plastic backing film which is laminated to a transparent, fragrance-emitting face film, the rear surface of the backing film being adhered to a bathroom or kitchen tile whereby the artwork is effectively sandwiched between the backing and face film and is thereby protectively shielded.

Briefly stated, these objects are attained in a replaceable air freshener primarily for use on the tiled wall of a bathroom or kitchen. The air freshener is formed by a transparent plastic face film laminated to a transparent plastic backing film to create a laminate whose dimensions match those of a standard tile. The rear surface of the backing film has a low tack, clear adhesive thereon whereby the laminate may be adhered to a selected tile on the wall or readily removed therefrom. The face film is constituted by a polymeric matrix having myriad cells dispersed therein impregnated with a volatile fragrance which is slowly released from the face film into the atmosphere of the room. Screened on the front surface of the backing film is an artwork which is visible through the face film and has a background field imparted thereto by the color of the tile onto which the laminate is adhered so that the artwork is then in harmony with the tiled wall. The emitted fragrance from the face film is thematically related to the artwork so that should the artwork be an Xmas tree, the fragrance will be that of pine.

OUTLINE OF DRAWINGS

For a better understanding of the invention as well as other objects and further features thereof, reference is made to the following detailed description to be read in conjunction with the accompanying drawings, wherein.

DESCRIPTION OF INVENTION

Figure 1:
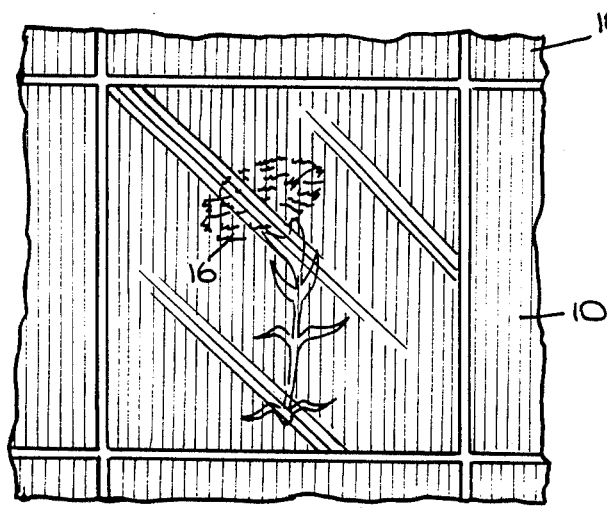
FIG. 1 shows an air freshener film laminate square in accordance with the invention mounted on a tile.

Referring now to FIG. 1, there is shown a tiled wall composed of an array of ceramic or composition tiles 10 having a smooth or glazed surface. This surface has a solid color, such as white, blue, green, etc. Such tiled walls are typically found in bathrooms, kitchens and in other environments where the need exists for an air freshener to render the atmosphere more pleasing.

Figure 2:
FIG. 2 shows the laminate with its face film cut away to expose the backing film.
Figure 3:
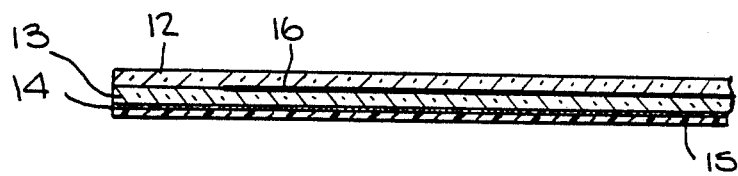
FIG. 3 is a section taken through the laminate.
Figure 4:
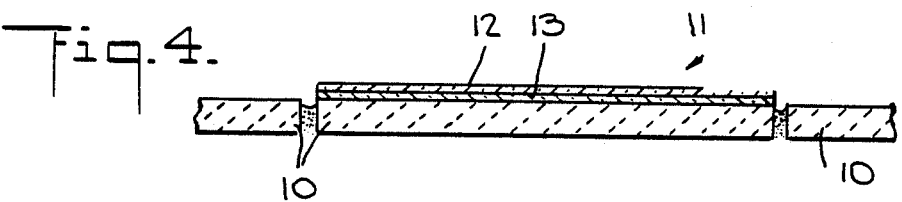
FIG. 4 is a section taken through a ceramic tile having the air freshener laminate adhered thereto.

Adhered to any one of tiles 10 is an air freshener laminate, generally designated by numeral 11. This laminate, as shown in FIGS. 2 and 3, takes the form of a flexible, transparent, rectangular or square face film 12 impregnated with a volatile fragrance in a relatively high concentration, preferably 20 to 30%. Laminated to the face film is a flexible transparent backing film 13 of the same dimensions. The dimensions of the film laminate match those of tile 10; hence when adhered to the tile, the color of the tile is seen through the laminate and a viewer is not aware of its presence.

The fragrance-emitting face film 12 may be of any known type and is preferably made of a bi-axially oriented polymeric material such as EVA (ethylene vinyl acetate) so that it is non-stretchable in either direction. The face film thickness, which may be of about three to six mils, determines the fragrance-emitting capacity of the air freshener. In practice, the laminate is protectively covered on both faces thereof with release sheets which are peeled off only before the film is adhered to the tile so that no loss of fragrance is experienced during storage.

The backing film 13 is made of a transparent flexible plastic material such as Mylar (polyester). It is laminated to the face film 12 by heat and pressure or by other means which will not impair the transparency of the laminate.

The rear surface of backing film 13 is coated with a clear, low-tack, pressure-sensitive adhesive layer 14 such as that used by 3M on its "Post-Em" sheets. Hence the laminate can be easily removed from the film when its fragrance is exhausted after a few weeks and replaced by a fresh laminate. A release sheet 15 as shown in FIG. 3 protectively covers adhesive layer 14, this sheet being peeled off when the laminate is to be adhered to a tile.

Screened or otherwise imprinted on the front surface of backing film 13 is a work of art 16 which in the example shown is a carnation flower. Because the artwork is effectively sandwiched between the face film and the backing film, it is protectively sealed in the laminate, yet it is clearly visible through the face film. The fragrance impregnated in face film 12 in this instance is a carnation fragrance so that the viewer not only sees a carnation but at the same time smells this flower. It is not essential to the invention that there be a match between the artwork and the fragrance, but only that the two be thematically related.

Thus, should the artwork be that of an ocean-going luxury liner, the fragrance may be that of a sea breeze; and should the artwork be that of wood burning in a fireplace, the thematically related fragrance may be a fragrant mixture suggesting a fireplace. Or in the case of an artwork showing a basket of different fruits, the aroma can be that of a bouquet of fruit fragrances.

In practice, the artwork may be a reproduction of a known masterpiece, such as Monet's classing painting of water lillies, in which case the fragrance would be that of lillies. The world of art is replete with paintings of organic objects such as flowers, trees, vegetables, etc., which have characteristic odors, and by screening these works on the films emitting thematically related fragrances, one then provides an air freshener which not only renders the ambient air more pleasing but also affords the occupant of the room with a work of art whose visual impression is enhanced by a thematically-related olfactory impression.

Figure 5:
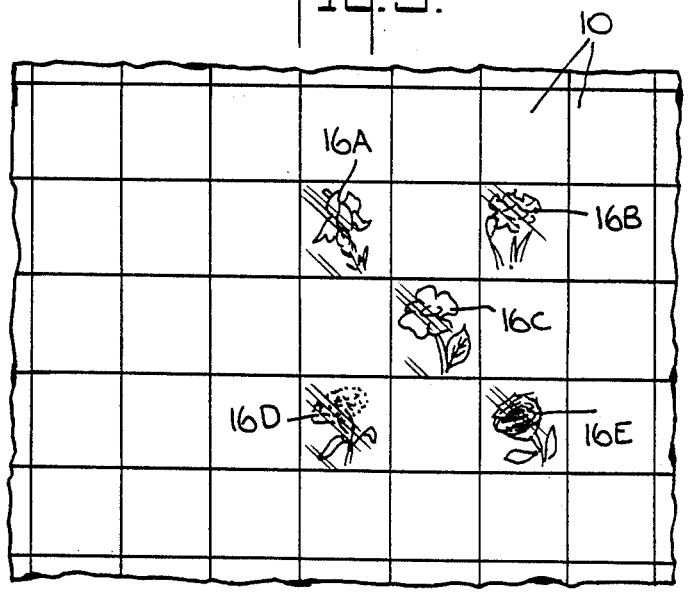
FIG. 5 shows a tiled wall on which is applied a pattern of air freshener laminates.

The air freshener laminate in accordance with the invention lends itself to creative selective grouping on the part of the user. Thus, as shown in FIG. 5, one may apply to selected tiles 10 in any array of tiles on a tiled wall, a geometric pattern of five air fresheners having different artworks 16A to 16E therein. Each work can, for example, represent a different flower, and each film will then emit an aroma related to the flower screened thereon. In this way, the user is able to create a bouquet of flowers and a corresponding bouquet of aromas.

It is important to note that the artwork embedded in the transparent laminate is imposed on a field which is the color of the underlying tile. Thus, if the tile color is green and the work of art is a rose flower, the flower is seen against a green field. Since the tiled wall is green and the laminated tile is also seen as green since the film is transparent, the laminated tile does not introduce a discordant note in the wall, and the work of art appears to be imposed on the wall, not on a blank space in the wall.

The laminate may, in practice, be applied to surfaces other than tiles. Thus, one may place the film on the window of an automobile and thereby render the interior atmosphere thereof more pleasing. The fragrance emitted in this instance may be a stimulant to discourage the driver from falling asleep at the wheel. Or one can adhere the film laminate to the corner of the glass window-door of a bathroom cabinet or on a room window.

While there has been shown and described a preferred embodiment of a film type air freshener in accordance with the invention, it will be appreciated that many changes and modifications may be made therein without, however, departing from the essential spirit thereof.

I claim:

1. An air freshener adherable to a wall tile or other substrate comprising a transparent laminate constituted by a transparent plastic face film inpregnated with a volatile fragrance that is slowly released therefrom, the fragrance being in a concentration resulting in a relatively prolonged emission and a transparent backing film laminated to said face film in a manner which does not impair the transparency of the laminate, the front surface of the backing film having an artwork imprinted thereon which is effectively sandwiched between the face film and the backing film and thereby protectively sealed, and a low-tack, pressure-sensitive, clear adhesive layer on the rear surface of the backing film whereby the laminate may be adhered onto a smooth substrate and later pulled therefrom when the fragrance is exhausted, the surface of the substrate being visible through the laminate.

2. An air freshener as set forth in claim 1, wherein said fragrance is thematically related to the artwork.

3. An air freshener as set forth in claim 1, wherein said backing film and said face film each have a thickness in the range of about three to six mils.

4. An air freshener as set forth in claim 2, wherein said artwork has a floral subject matter, and the fragrance is a floral aroma.

5. An air freshener as set forth in claim 1 in combination with a wall tile having a smooth surface wherein said laminate is of substantially the same dimensions as said tile and is adhered to said surface.

6. The combination as set forth in claim 5, wherein said tile is a ceramic tile having a glazed surface.

7. The combination as set forth in claim 5, wherein said tile surface has a solid color and effectively forms a ground field for said artwork.

* * * * *